(12) United States Patent
Park et al.

(10) Patent No.: US 10,945,907 B2
(45) Date of Patent: Mar. 16, 2021

(54) MOTION ASSISTANCE APPARATUS

(71) Applicant: Samsung Electronics Co., Ltd., Suwon-si (KR)

(72) Inventors: Youngjin Park, Seoul (KR); Jongwon Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 388 days.

(21) Appl. No.: 15/967,878

(22) Filed: May 1, 2018

(65) Prior Publication Data

US 2019/0142680 A1 May 16, 2019

(30) Foreign Application Priority Data

Nov. 15, 2017 (KR) .................. 10-2017-0152481

(51) Int. Cl.
| | | |
|---|---|---|
| *A61H 1/02* | (2006.01) | |
| *A61H 3/00* | (2006.01) | |
| *A61F 5/01* | (2006.01) | |

(52) U.S. Cl.
CPC ......... *A61H 1/0262* (2013.01); *A61F 5/0102* (2013.01); *A61F 5/0123* (2013.01); *A61H 3/00* (2013.01); *A61F 2005/0155* (2013.01); *A61F 2005/0165* (2013.01); *A61H 2003/007* (2013.01); *A61H 2201/1642* (2013.01); *A61H 2201/1652* (2013.01); *A61H 2201/5007* (2013.01); *A61H 2201/5053* (2013.01); *A61H 2201/5064* (2013.01)

(58) Field of Classification Search
CPC ............... A61F 5/0102; A61F 5/0123; A61F 2005/0155; A61F 2005/0165; A61F 2002/6863; A61F 2002/701; A61F 2002/704; A61F 5/01; A61H 1/0262; A61H 3/00; A61H 2003/007; A61H 2201/1642; A61H 2201/1652; A61H 2201/5007; A61H 2201/5053; A61H 2201/5064; A61H 1/00; B25J 9/0006

USPC .............................. 601/5, 34; 602/16, 23, 26
See application file for complete search history.

(56) References Cited

U.S. PATENT DOCUMENTS

| | | | |
|---|---|---|---|
| 5,020,790 A * | 6/1991 | Beard ................... | A61F 5/0102 482/4 |
| 2007/0010378 A1 | 1/2007 | Katoh et al. | |
| 2013/0006159 A1 | 1/2013 | Nakashima et al. | |
| 2014/0012164 A1 | 1/2014 | Tanaka | |
| 2015/0005686 A1* | 1/2015 | Kazerounian ......... | A61F 5/0123 602/16 |

(Continued)

FOREIGN PATENT DOCUMENTS

| | | |
|---|---|---|
| JP | 2014073199 A | 4/2014 |
| KR | 20-0419809 Y1 | 6/2006 |

(Continued)

*Primary Examiner* — Tu A Vo
*Assistant Examiner* — Alexander Morales
(74) *Attorney, Agent, or Firm* — Harness, Dickey and Pierce, P.L.C.

(57) ABSTRACT

A motion assistance apparatus including a support link to be attached to a waist of a user, a thigh link connected to a first end of the support link, a knee link connected to a first end of the thigh link, a connecting link connected to a first end of the knee link, and selectively connected to a second end of the support link, and an actuator configured to rotate the knee link with respect to the thigh link is provided.

19 Claims, 16 Drawing Sheets

(56) References Cited

U.S. PATENT DOCUMENTS

| | | | |
|---|---|---|---|
| 2016/0262969 A1* | 9/2016 | Ohta | A61H 1/0262 |
| 2016/0287423 A1* | 10/2016 | Ramirez | A61F 2/68 |
| 2016/0338897 A1 | 11/2016 | Takenaka et al. | |
| 2016/0374887 A1* | 12/2016 | Wu | A61F 5/0127 |
| | | | 623/31 |
| 2016/0374888 A1* | 12/2016 | Tung | A61H 1/024 |
| | | | 623/24 |
| 2017/0231797 A1* | 8/2017 | LeCursi | A61F 5/0127 |
| | | | 602/16 |

FOREIGN PATENT DOCUMENTS

| | | |
|---|---|---|
| KR | 20090124559 A | 12/2009 |
| KR | 20120130975 A | 12/2012 |
| KR | 20150041361 A | 4/2015 |
| KR | 20160110590 A | 9/2016 |

\* cited by examiner

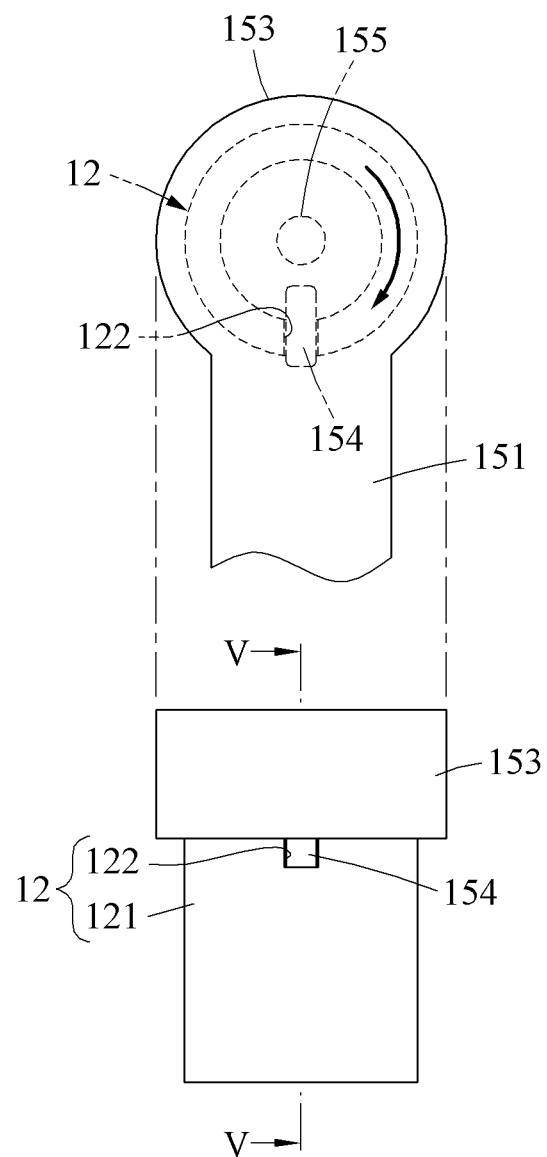

MOTION ASSISTANCE APPARATUS

CROSS-REFERENCE TO RELATED APPLICATION

This application claims under 35 U.S.C. § 119 to Korean Patent Application No. 10-2017-0152481, filed on Nov. 15, 2017, in the Korean Intellectual Property Office, the entire contents of which are incorporated herein by reference in their entirety.

BACKGROUND

1. Field

At least one example embodiment relates to a motion assistance apparatus.

2. Description of the Related Art

With the onset of rapidly aging societies, an increasing number of people may experience inconvenience and/or pain from joint problems. Thus, there may be a growing interest in walking assistance apparatuses enabling the elderly and/or patients having joint problems to walk with less effort.

SUMMARY

Some example embodiments relate to a motion assistance apparatus.

In some example embodiments, the motion assistance apparatus includes a support link configured to attach to a waist of a user, the support link including a first end and a second end; a thigh link connected to the first end of the support link; a knee link connected to the thigh link; a connecting link connected to the knee link, the connecting link configured to selectively connect to the second end of the support link; and an actuator configured to rotate the knee link with respect to the thigh link.

In some example embodiments, the connecting link is configured to, assist a hip joint motion of the user by performing a 4-bar linkage motion together with the thigh link, the knee link, and the support link, if the connecting link is connected to the support link, and assist a knee joint motion of the user, if the connecting link is disconnected from the support link.

In some example embodiments, the motion assistance apparatus further includes a calf supporting frame rotatably connected to the connecting link, the calf supporting frame configured to support a calf of the user, if the connecting link is disconnected from the support link.

In some example embodiments, the connecting link includes a stopper configured to restrict a rotation range of the calf supporting frame.

In some example embodiments, the calf supporting frame is configured to, rotate between a first state and a second state, the first state being a state in which the calf supporting frame is in contact with a first side of the stopper and the second state being a state in which the calf supporting frame is in contact with a second side of the stopper, and maintain the first state of being in contact with the first side of the stopper, if the calf supporting frame is supporting a calf of the user while the connecting link is disconnected from the support link.

In some example embodiments, the calf supporting frame is curved such that the calf supporting frame is configured to enclose the calf of the user, if the calf supporting frame is in contact with the calf of the user.

In some example embodiments, the support link includes a first sub-support link configured to attach to the waist of the user, the first sub-support link rotatably connected to a first portion of the thigh link; a second sub-support link having a first end and a second end, the second sub-support link being between the first sub-support link and the knee link, the first end of the second sub-support link being rotatably connected to a second portion of the thigh link; and a third sub-support link configured to connect the first sub-support link and the second sub-support link, wherein the connecting link is configured to selectively connect to the second end of the second sub-support link.

In some example embodiments, when the connecting link is connected to the second end of the second sub-support link, the first sub-support link, the second sub-support link, and the knee link are in parallel with each other, the third sub-support link is in parallel with the thigh link, and the connecting link is in parallel with the thigh link.

In some example embodiments, the actuator includes a driving source on the thigh link such that the driving source is closer to the support link than the knee link; and a power transmitting member configured to transmit power from the driving source to the knee link.

In some example embodiments, the support link includes a coupling pin configured to rotatably connect the connecting link to the support link, and the connecting link includes a connecting head opened toward the coupling pin, and wherein the motion assistance apparatus further includes a fixing pin configured to attach to the connecting head, the fixing pin configured to resist a separation of the coupling pin from the connecting head.

In some example embodiments, the connecting head further includes a projection protruding toward the coupling pin, and the coupling pin includes a fixing groove configured to receive the fixing pin and the projection.

In some example embodiments, a first one of the knee link and the connecting link includes a receiver, the receiver having a dent shape, and a second one of the knee link and the connecting link includes a protrusion, the protrusion configured to be inserted into the receiver.

In some example embodiments, the protrusion is configured to align with the receiver, if the connecting link is disconnected from the support link and rotates at least a set angle with respect to the knee link.

In some example embodiments, the one of the knee link and the connecting link further includes a link axis configured to pass through the second one of the knee link and the connecting link; a support plate at an end portion of the link axis; and an elastic body between the support plate and an inner wall of the second one of the knee link and the connecting link.

Some example embodiments relate to a motion assistance apparatus.

In some example embodiments, the motion assistance apparatus includes a support link configured to attach to a waist of a user, the support link including a first end and a second end; a thigh link connected to the first end of the support link; a knee link connected to the thigh link; a connecting link connected the knee link, the connecting link configured to selectively connect to the second end of the support link; a first actuator configured to rotate the knee link with respect to the thigh link; and a second actuator configured to rotate the thigh link with respect to the support link.

In some example embodiments, the first actuator and the second actuator are configured to assist one or more of flexion motion and an extension motion of a hip joint of the user, if the connecting link is connected to the support link.

In some example embodiments, the motion assistance apparatus further includes a calf supporting frame connected to the connecting link, the calf supporting frame configured to support a calf of the user, if the connecting link is disconnected from the support link.

In some example embodiments, when the connecting link is disconnected from the support link, the first actuator is configured to assist one or more of a flexion motion and an extension motion of a knee joint of the user, and the second actuator is configured to assist one or more of a flexion motion and an extension motion of a hip joint of the user.

Some example embodiments relate to a motion assistance apparatus.

In some example embodiments, the motion assistance apparatus includes a support link configured to attached to a waist of a user, the support link including a first end and a second end; a thigh link connected to the first end of the support link; a knee link connected to the thigh link; and a connecting link connected to the knee link, the connecting link configured to selectively connect to the second end of the support link, wherein the motion assistance apparatus is configured to select which joint of the user is to receive an assistance force based on whether the connecting link is connected to the support link.

In some example embodiments, the motion assistance apparatus is configured to, transmit the assistance force to a hip joint, if the connecting link is connected to the support link, and transmit the assistance force to a knee joint, if the connecting link is disconnected from the support link.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 9A illustrates a knee link and a connecting link being fixed according to at least one example embodiment;

DETAILED DESCRIPTION

Figure 1:
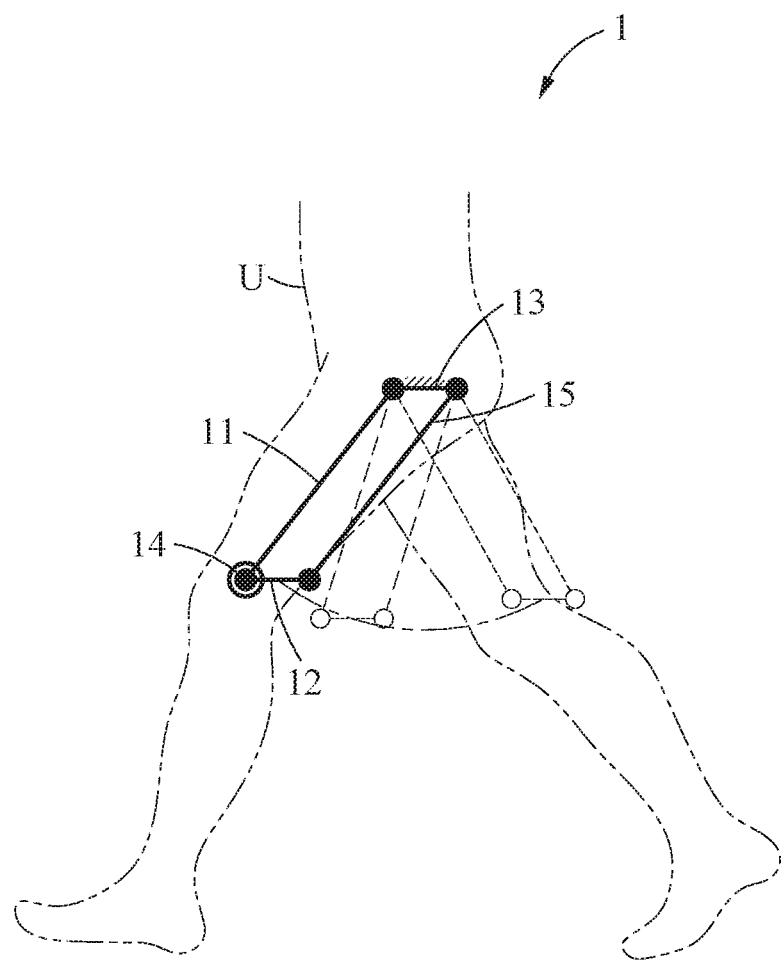
FIG. 1 illustrates a motion assistance apparatus assisting a hip joint of a user according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

FIG. 1 illustrates a motion assistance apparatus assisting a hip joint of a user according to at least one example embodiment.

Referring to FIG. 1, a motion assistance apparatus 1 may be worn by a user U to assist a motion of the user U. The user U may correspond to a human, an animal, or a robot. However, the user U is not limited thereto. The motion assistance apparatus 1 may include a thigh link 11, a knee link 12, a support link 13, an actuator 14, and a connecting link 15.

The thigh link 11, the knee link 12, the support link 13 and the connecting link 15 may construct a 4-bar linkage. The support link 13 may be attached to a waist of the user U. The thigh link 11, the knee link 12, the support link 13 and the connecting link 15 may perform a 1-degree of freedom (DOF) motion.

The actuator 14 may adjust an angle between the thigh link 11 and the knee link 12. For example, the actuator 14 may rotate the knee link 12 with respect to the thigh link 11.

In FIG. 1, when the actuator 14 rotates the knee link 12 clockwise with respect to the thigh link 11, the 4-bar linkage including the thigh link 11, the knee link 12, the support link 13 and the connecting link 15 may move counterclockwise and assist an extension motion of a hip joint.

When the actuator 14 rotates the knee link 12 counterclockwise with respect to the thigh link 11, the 4-bar linkage including the thigh link 11, the knee link 12, the support link 13 and the connecting link 15 may move clockwise and assist a flexion motion of the hip joint.

Figure 2:
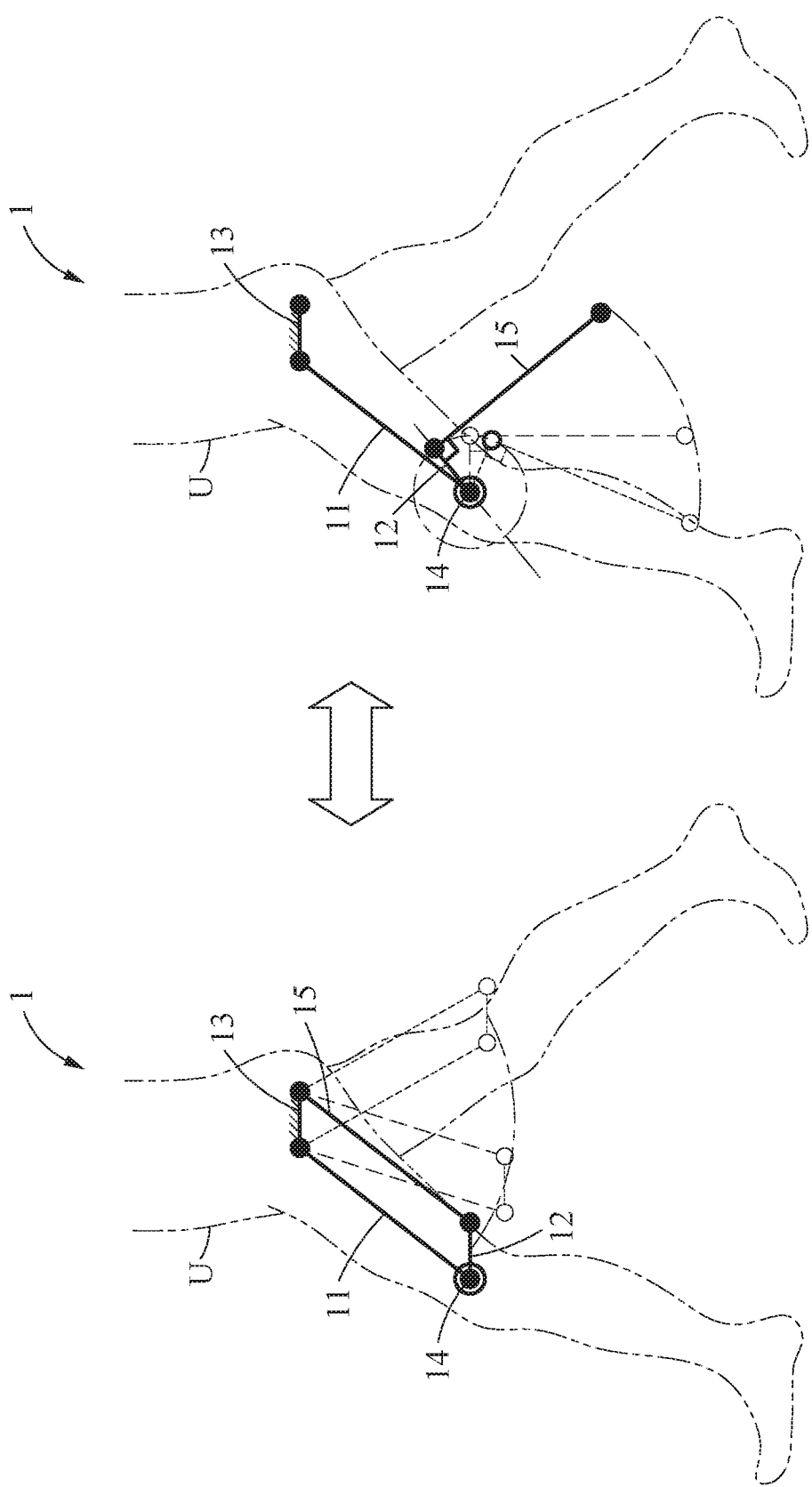
FIG. 2 illustrates a motion assistance apparatus selectively assisting a hip joint or a knee joint of a user according to at least one example embodiment.

FIG. 2 illustrates a motion assistance apparatus selectively assisting a hip joint or a knee joint of a user according to at least one example embodiment.

Referring to FIG. 2, the motion assistance apparatus 1 may selectively assist a hip joint or a knee joint. A left view of FIG. 2 illustrates the motion assistance apparatus 1 assisting a hip joint of the user U, and a right view of FIG. 2 illustrates the motion assistance apparatus 1 assisting a knee joint of the user U.

When the thigh link 11, the knee link 12, the support link 13 and the connecting link 15 of the motion assistance apparatus 1 operate as a 4-bar linkage, the motion assistance apparatus 1 may perform a 1-DOF motion. Thus, power applied from the actuator 14 to the knee link 12 may be used to assist a flexion or extension motion of the hip joint of the user U.

When the thigh link 11, the knee link 12, the support link 13 and the connecting link 15 of the motion assistance apparatus 1 do not construct a 4-bar linkage and are disconnected, the motion assistance apparatus 1 may perform a one or higher-DOF motion. For example, when the connecting link 15 is disconnected from the support link 13, the thigh link 11 may perform a rotary motion with respect to the support link 13, and the knee link 12 may perform a relative rotary motion with respect to the thigh link 11. Further, when a relative angle between the knee link 12 and the connecting link 15 is fixed, the power applied from the actuator 14 to the knee link 12 may be used to assist a flexion or extension motion of the knee joint of the user U.

In FIG. 2, when the 4-bar linkage is disconnected and the actuator 14 rotates the knee link 12 clockwise with respect to the thigh link 11, the knee link 12 and the connecting link 15 may move clockwise and assist the extension motion of the knee joint.

When the user U requires an assistance force for the hip joint, the motion assistance apparatus 1 may operate in a hip joint assistance mode. When the user U requires an assistance force for the knee joint, the motion assistance apparatus 1 may operate in a knee joint assistance mode. The motion assistance apparatus 1 may switch between the hip joint assistance mode or the knee joint assistance mode based on whether the connecting link 15 is connected to the support link 13.

For example, when the user U performs a level walking, the hip joint may require a relatively greater force and/or torque than the knee joint. In this example, the motion assistance apparatus 1 may operate in the hip joint assistance mode. When the user U performs a motion of climbing a sloping hill or standing up, the knee joint may require a relatively greater force and/or torque than the hip joint. In this example, the motion assistance apparatus 1 may operate in the knee joint assistance mode.

Figure 3:
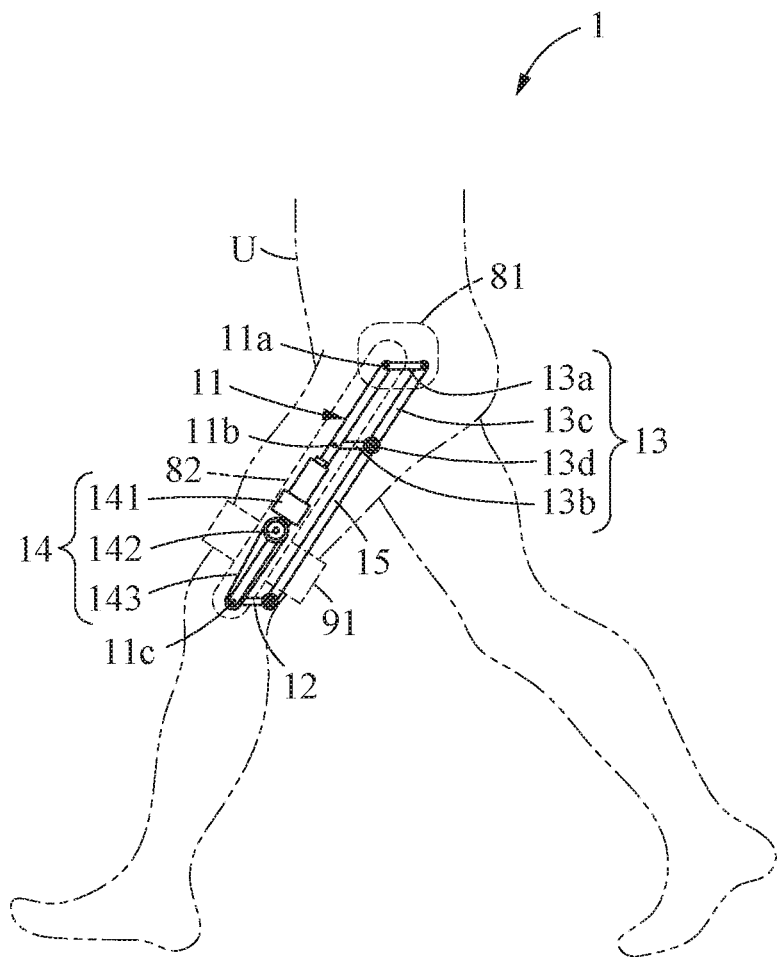
FIG. 3 is a side view illustrating a motion assistance apparatus assisting a hip joint of a user according to at least one example embodiment.
Figure 4:
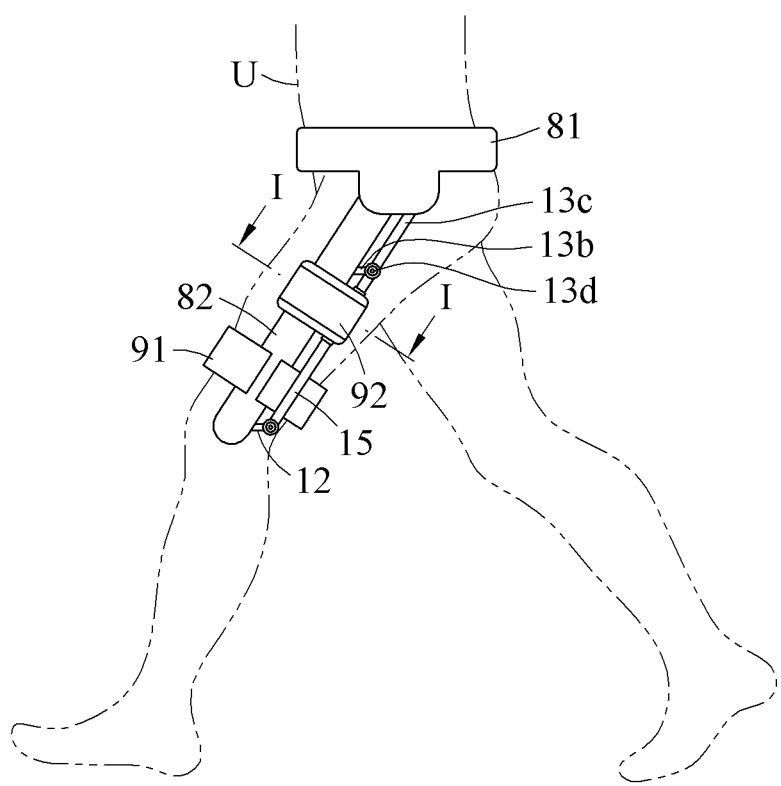
FIG. 4 is a side view illustrating a motion assistance apparatus according to at least one example embodiment.
Figure 5:
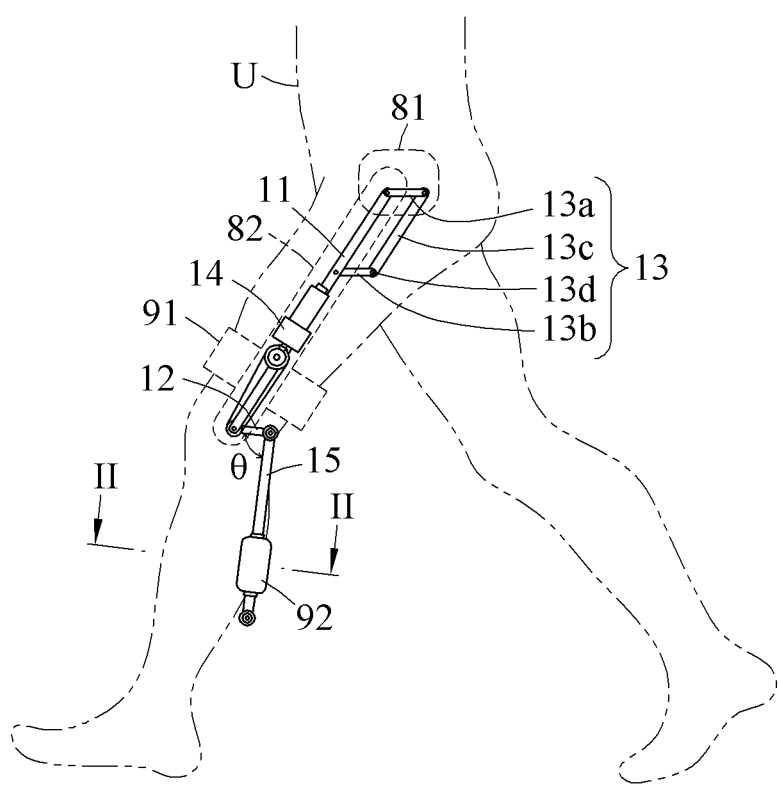
FIG. 5 is a side view illustrating a motion assistance apparatus assisting a knee joint of a user according to at least one example embodiment.

FIG. 3 is a side view illustrating a motion assistance apparatus assisting a hip joint of a user according to at least one example embodiment, FIG. 4 is a side view illustrating the motion assistance apparatus according to at least one example embodiment, and FIG. 5 is a side view illustrating the motion assistance apparatus assisting a knee joint of the user according to at least one example embodiment.

Referring to FIGS. 3 through 5, the motion assistance apparatus 1 may include the thigh link 11, the knee link 12, the support link 13, the actuator 14, the connecting link 15, a waist frame 81, a thigh frame 82, a thigh attachable portion 91, and a calf supporting frame 92.

The thigh link 11 may be rotatably connected to a first end of the support link 13. The thigh link 11 may be in parallel with a thigh of the user U. The thigh link 11 may perform a rotary motion with respect to the support link 13, thereby assisting a flexion motion and/or an extension motion of the thigh of the user U about the hip joint. A distance between both ends of the thigh link 11 may be approximately equal to a length of the thigh of the user U. A distance between a first point 11a at which the thigh link 11 is connected to the support link 13 and a third point 11c at which the thigh link 11 is connected to the knee link 12 may be approximately equal to the length of the thigh of the user U. When viewed from a side of the user U, that is, as in FIG. 3, the first point 11a of the thigh link 11 may overlap the hip joint of the user U, and the third point 11c of the thigh link 11 may overlap the knee joint of the user U. For example, the thigh link 11 may include a length adjusting device (not shown) configured to adjust a length of the thigh link 11 based on a body size of the user, in particular, the length of the thigh. The length adjusting device may alleviate misalignments between joints of the motion assistance apparatus 1 and joints of the user U.

The knee link 12 may be rotatably connected to a first end of the thigh link 11. The knee link 12 may rotate relative to the thigh link 11 by the actuator 14. For example, the knee link 12 may include a pulley or sprocket (not shown) at a portion thereof connected to the thigh link 11 to receive power from the actuator 14. The knee link 12 may be provided from the thigh link 11 toward a rear side of the user U.

The support link 13 may be attached to a waist of the user U. The support link 13 may include a first sub-support link 13a, a second sub-support link 13b, a third sub-support link 13c, and a coupling pin 13d.

The first sub-support link 13a may be attached to the waist of the user U. For example, the first sub-support link 13a may be provided in the waist frame 81 that is attachable to and detachable from the waist of the user U. The first sub-support link 13a may be rotatably connected to the first point 11a of the thigh link 11. For example, the first sub-support link 13a may be in parallel with the knee link 12.

A first end of the second sub-support link 13b may be rotatably connected to a second point 11b of the thigh link 11. The second sub-support link 13b may be below the first sub-support link 13a. The second sub-support link 13b may be rotatably connected to a first end of the connecting link 15. The second sub-support link 13b may be positioned such that the calf supporting frame 92 may support a relatively large-area portion of a calf of the user U, that is, a relatively thick portion of the calf of the user U. For example, as a distance between the second point 11b and the first point 11a increases, a distance between the second sub-support link 13b and the knee link 12 may decrease and a distance between both ends of the connecting link 15 may decrease. When the connecting link 15 rotates clockwise in the example of FIG. 3 and is in parallel with the calf of the user U (see FIG. 5), the calf supporting frame 92 may move upward.

The third sub-support link 13c may connect the first sub-support link 13a and the second sub-support link 13b. For example, a first end of the third sub-support link 13c may be rotatably connected to the first sub-support link 13a, and a second end of the third sub-support link 13c may be rotatably connected to the second sub-support link 13b.

When the connecting link 15 is connected to the second sub-support link 13b, the first sub-support link 13a, the second sub-support link 13b and the knee link 12 may be in parallel, and the third sub-support link 13c and the thigh link 11 may be in parallel. Further, the connecting link 15 and the thigh link 11 may be in parallel. In this example, a 4-bar linkage including the first sub-support link 13a, the second sub-support link 13b, the third sub-support link 13c and the thigh link 11 may move in conjunction with a 4-bar linkage including the second sub-support link 13b, the knee link 12, the connecting link 15 and the thigh link 11. Although FIGS. 3 and 4 illustrate the connecting link 15 and the third sub-support link 13c being in parallel, example embodiments are not limited thereto. For example, when the 4-bar linkage including the first sub-support link 13a, the second sub-support link 13b, the third sub-support link 13c and the thigh link 11 and the 4-bar linkage including the second sub-support link 13b, the knee link 12, the connecting link 15 and the thigh link 11 each form a parallelogrammic structure, the two 4-bar linkages may move in conjunction with each other.

The coupling pin 13d may be provided in the first end of the second sub-support link 13b or the third sub-support link 13c. The connecting link 15 may be rotatably connected to the coupling pin 13d.

The actuator 14 may rotate the knee link 12 with respect to the thigh link 11. The actuator 14 may include a driving source 141, a drive shaft 142, and a power transmitting member 143.

The driving source 141 may generate power to assist a joint motion of the user U. For example, the driving source 141 may be a motor. The driving source 141 may be on one of the thigh link 11 and the knee link 12. Although FIGS. 3 through 5 illustrate the driving source 141 being on the thigh link 11, a position of the driving source 141 is not limited thereto. Hereinafter, for ease of description, description will be provided based on an example in which the driving source 141 is on the thigh link 11. The driving source 141 may be closer to the support link 13 than the knee link 12. In this example, an inertial moment of the motion assistance apparatus 1 may decrease. Although FIG. 3 illustrates the driving source 141 being connected to a central portion of the thigh link 11, the driving source 141 may be positioned closer to a portion above the thigh link 11, that is, the waist of the user U.

The drive shaft 142 may rotate using the power received from the driving source 141. For example, the drive shaft 142 may protrude from the driving source 141 toward a joint connecting the thigh link 11 and the knee link 12. In this example, a distance between the drive shaft 142 and the joint connecting the thigh link 11 and the knee link 12 may decrease.

The power transmitting member 143 may transmit the power received from the driving source 141 to the knee link 12. For example, the power transmitting member 143 may be a band, belt or chain with a first side wound over the drive shaft 142 and a second side wound over at least a portion of the knee link 12.

The motion assistance apparatus 1 may further include a controller (not shown) that includes memory and processing circuitry.

The memory may include at least one of a volatile memory, non-volatile memory, random access memory (RAM), a flash memory, a hard disk drive, and an optical disk drive.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design or execution of computer readable instructions stored in a memory (not shown), as a special purpose computer to control the actuator 14.

For example, the processing circuitry may be configured to control the driving source 141 to generate the power to rotate the drive shaft 142 such that the generated power is transmitted to the knee link 12.

In some example embodiments, the processing circuitry may also be configured to control the connection mechanism of the connecting link 15 to selectively latch the connecting link 15 to the support link 13 or the knee link 12 based on whether the motion assistance apparatus 1 is operating in the hip joint assistance mode or the knee joint assistance mode.

Figure 8A:
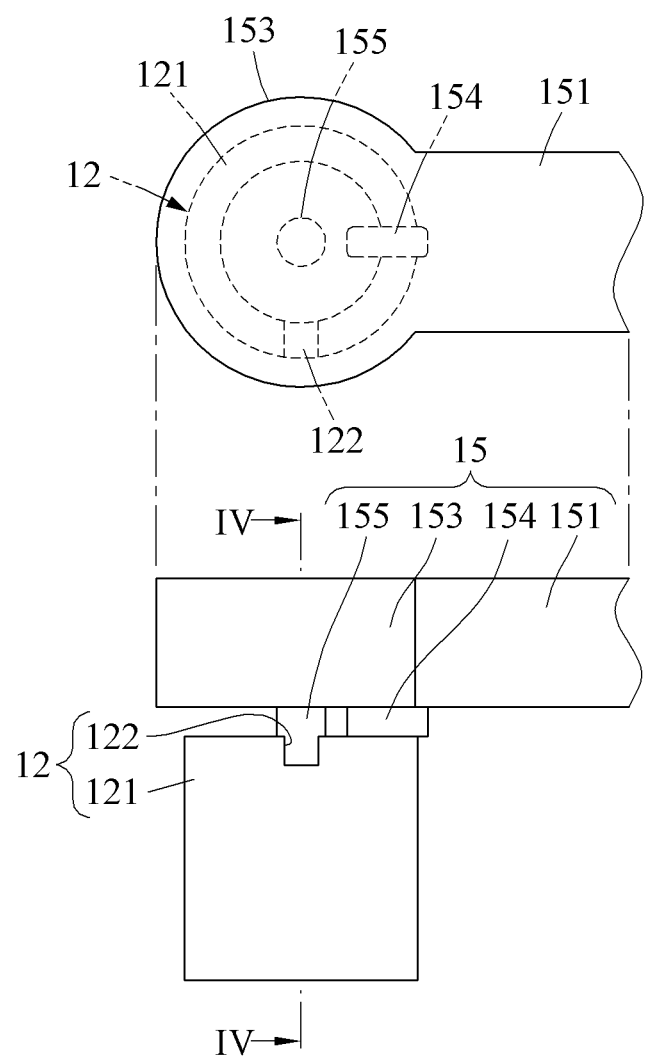
FIG. 8A illustrates a knee link and a connecting link being rotatable relative to each other according to at least one example embodiment.

For example, the connecting link 15 may be connected to the support link 13 via an electromagnet rather than fixing pin 70 (see FIGS. 6A and 6B), and the processing circuitry may selectively activate or deactivate the electromagnet to connect the connecting link 15 to the support link 13. Further, the processing circuitry may rotate the connecting link 15 at least a set angle such that, as illustrated in FIGS. 8A and 9A, a protrusion 154 is inserted into a receiver 122 to connect the connecting link 15 to the support link 13.

In some example embodiments, the processing circuitry may be connected to one or more sensors (not shown), and receive sensor data from the one or more sensors to determine whether the user is walking level, performing the motion of climbing the sloping hill or standing up, and may control the motion assistance apparatus 1 based on a result of the sensing.

For example, the processing circuitry may set the motion assistance apparatus 1 into one of the hip joint assistance mode or the knee joint assistance mode based on the result of the sensing such that the controller selectively latches connecting link 15 to the support link 13 in response to the sensor data indicating that the user is walking level, and decouples the connecting link 15 from the support 13 in response to the sensor data indicating that the user is climbing the sloping hill or standing up.

Further still, in some example embodiments, the processing circuitry may be configured to adjust the length of the thigh link 11 by controlling the length adjusting device (not shown) to expand or contract based on the body size of the user, in particular, the length of the thigh of the user, which may be input by the user.

The first end of the connecting link 15 may be maintained to be rotatably connected to the knee link 12, and a second end of the connecting link 15 may be selectively connected to the support link 13. FIG. 3 illustrates the connecting link 15 being rotatably connected to the support link 13. In this example, in a state of being connected to the support link 13, the connecting link 15 may perform a 4-bar linkage motion together with the thigh link 11, the knee link 12 and the support link 13, and assist a hip joint motion of the user U. Meanwhile, FIG. 5 illustrates the connecting link 15 being disconnected from the support link 13. When the connecting link 15 rotates at least a desired (or, alternatively, a preset) angle, the connecting link 15 may be connected to the knee link 12. When the motion assistance apparatus 1 is in the knee joint assistance mode, the connecting link 15 and the knee link 12 being connected may maintain a desired (or, alternatively, a predetermined) angle θ. The connecting link 15 may assist a knee joint motion of the user U together with the knee link 12.

The waist frame 81 may be attached to the waist of the user U. For example, the waist frame 81 may enclose the waist of the user U, and a circumference of the waist frame 81 may be adjusted to fit the waist of the user U. The waist frame 81 may receive at least a portion of the support link 13 therein. For example, the waist frame 81 may receive the first sub-support link 13*a*.

The thigh frame 82 may be attached to the thigh of the user U. The thigh frame 82 may include the thigh attachable portion 91 configured to enclose the thigh of the user U. The circumference of the thigh attachable portion 91 may be adjusted to fit the thigh of the user U. The thigh frame 82 may receive at least a portion of the thigh link 11. The thigh frame 82 may cover the actuator 14, and prevent an inflow of an external foreign substance into the actuator 14.

The calf supporting frame 92 may be rotatably connected to the connecting link 15. When the motion assistance apparatus 1 is in the knee joint assistance mode such that the connecting link 15 is disconnected from the support link 13, the calf supporting frame 92 may support the calf of the user U. In a case in which the motion assistance apparatus 1 assists the knee joint of the user U, the calf supporting frame 92 may support the calf of the user U (see FIG. 5). In this example, the calf supporting frame 92 may assist an extension motion of the knee joint of the user U. Although not shown in the drawings, the calf supporting frame 92 may support a shank of the user U, thereby assisting a flexion motion of the knee joint of the user U. Further, the calf supporting frame 92 may include a calf attachable portion 92*a* (see FIG. 13) configured to enclose the calf of the user U. A circumference of the calf attachable portion 92*a* may be adjusted to fit the calf of the user U.

Figure 6A:
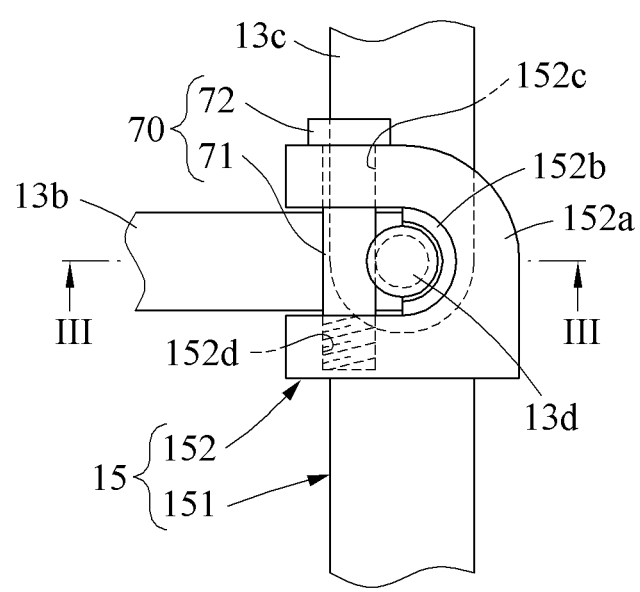
FIG. 6A is a side view illustrating a supporting link and a connecting link being connected according to at least one example embodiment.
Figure 6B:
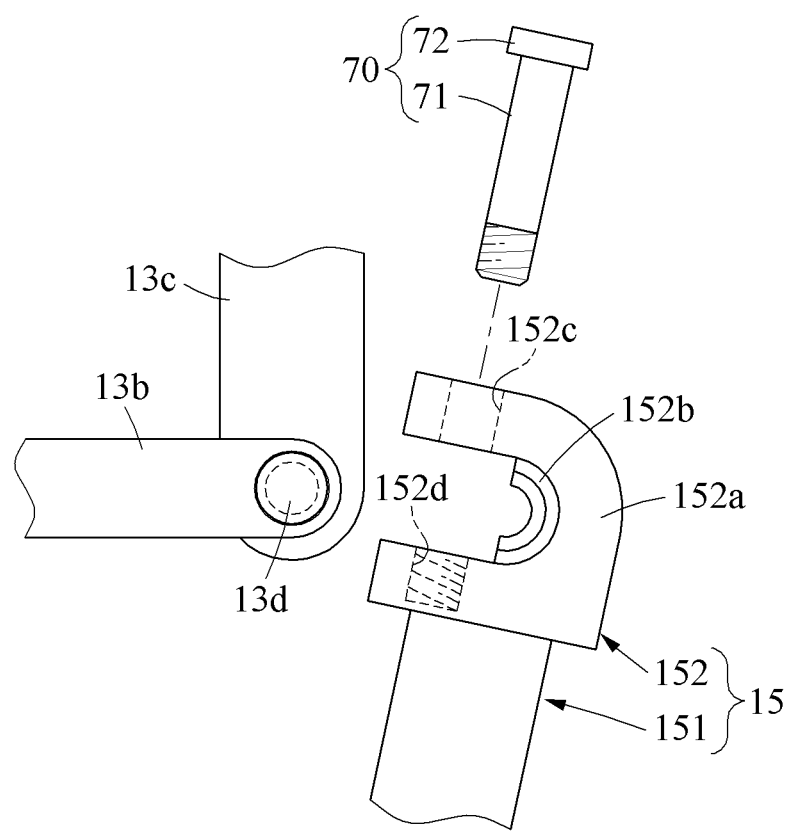
FIG. 6B is an exploded view illustrating a support link and a connecting link being disconnected according to at least one example embodiment.
Figure 7:
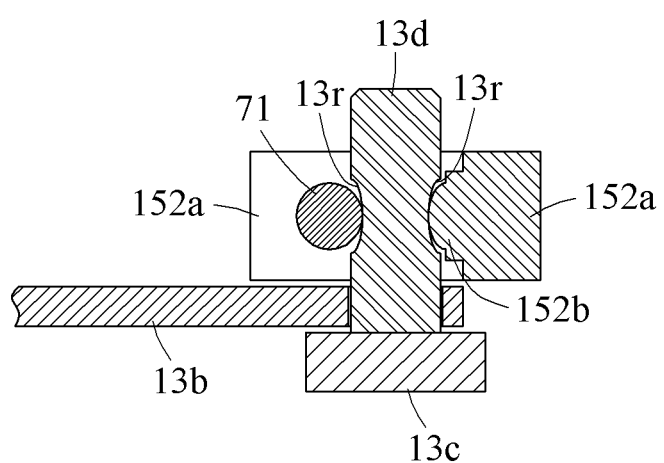
FIG. 7 is a cross-sectional view of the supporting link and the connecting link of FIG. 6A, cut along a line III-III.

FIG. 6A is a side view illustrating a supporting link and a connecting link being connected according to at least one example embodiment, FIG. 6B is an exploded view illustrating the support link and the connecting link being disconnected according to at least one example embodiment, and FIG. 7 is a cross-sectional view of the supporting link and the connecting link of FIG. 6A, cut along a line III-III.

Referring to FIGS. 6A through 7, the second sub-support link 13*b* and the third sub-support link 13*c* may relatively rotate about the coupling pin 13*d*. For example, the coupling pin 13*d* may protrude from a first side of the third sub-support link 13*c*, and the second sub-support link 13*b* may include a hole to receive the coupling pin 13*d*. The second sub-support link 13*b* may rotate about the coupling pin 13*d*.

The coupling pin 13*d* may rotatably connect the connecting link 15 to the support link 13. The connecting link 15 may be selectively connected to the coupling pin 13*d*. The connecting link 15 may include a connecting link body 151 which is a longitudinal member, a connecting head 152, and an opposing end portion 153.

The connecting head 152 may be at a first end of the connecting link body 151. The connecting head 152 may be opened toward the coupling pin 13*d*. For example, the connecting head 152 may be U-shaped. When the connecting link 15 rotates toward the coupling pin 13*d*, the coupling pin 13*d* may be received in the connecting head 152. The connecting head 152 may include a head base 152*a* connected to the connecting link body 151, a projection 152*b* protruding from an inner side of the head base 152*a*, a head hole 152*c* at an upper portion of the head base 152*a*, and a head recess 152*d* dent at a lower portion of the head base 152*a*.

The motion assistance apparatus 1 may further include a fixing pin 70 to be screwed into the connecting head 152. The fixing pin 70 may prevent a separation of the coupling pin 13*d* from the connecting head 152. For example, the fixing pin 70 may be screwed into the head hole 152*c* and the head recess 152*d*. The fixing pin 70 may include a fixing pin body 71 having a diameter equal to those of the head hole 152*c* and the head recess 152*d*, and a fixing pin plate 72 at a first end of the fixing pin body 71. The fixing pin plate 72 may have a greater diameter than the fixing pin body 71 such that the user U may easily screw the fixing pin 710. The fixing pin body 71 may include threads at a lower end portion, and the head recess 152*d* may include threads corresponding to the threads of the fixing pin body 71 such that the fixing pin body 71 may be screwed into the head recess 152*d*.

The coupling pin 13*d* may include a fixing groove 13*r* configured to receive the fixing pin 70 and the projection 152*b*. The fixing groove 13*r* may be formed along a circumference of the coupling pin 13*d*. The fixing groove 13*r* may prevent a sliding separation of the round fixing pin body 71 and the projection 152*b* from the coupling pin 13*d*. For example, the fixing groove 13*r* may have a concave shape with a curvature greater than or equal to those of the fixing pin body 71 and the projection 152*b*.

A connecting mechanism between the connecting link 15 and the support link 13 is not limited thereto. For example, the connecting link 15 and the support link 13 may be rotatably connected to or disconnected from each other by a clamp.

Figure 8B:
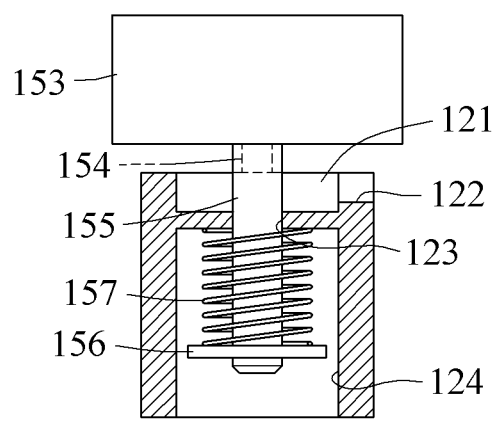
FIG. 8B is a cross-sectional view illustrating the knee link and the connecting link of FIG. 8A, cut along a line IV-IV.
Figure 9B:
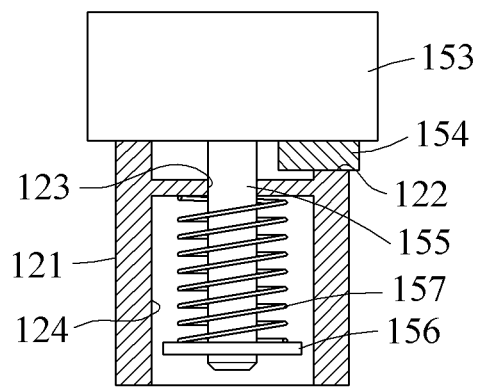
FIG. 9B is a cross-sectional view illustrating the knee link and the connecting link of FIG. 9A, cut along a line V-V.

FIG. 8A illustrates a knee link and a connecting link being rotatable relative to each other according to at least one example embodiment, and FIG. 8B is a cross-sectional view illustrating the knee link and the connecting link of FIG. 8A, cut along a line IV-IV. FIG. 9A illustrates a knee link and a connecting link being fixed according to at least one example embodiment, and FIG. 9B is a cross-sectional view illustrating the knee link and the connecting link of FIG. 9A, cut along a line V-V.

Referring to FIGS. 8A through 9B, the connecting link 15 may be relatively rotatably connected to the knee link 12 (FIGS. 8A and 8B), or may be fixed to the knee link 12 (FIGS. 9A and 9B). When the connecting link 15 constructs a 4-bar linkage together with the thigh link 11, the knee link 12 and the support link 13, the connecting link 15 may be relatively rotatably connected to the knee link 12. When the connecting link 15 is disconnected from the support link 13 and does not construct a 4-bar linkage together with the thigh link 11, the knee link 12 and the support link 13, the connecting link 15 may be fixed to the knee link 12.

One of the knee link 12 and the connecting link 15 may include a receiver having a dent shape, and the other one of the knee link 12 and the connecting link 15 may include a protrusion to be inserted into the receiver. For example, the knee link 12 may include a receiver 122 having a dent shape, and the connecting link 15 may include a protrusion 154 to be inserted into the receiver 122. The receiver 122 may have a width equal to that of the protrusion 154. Prior to detailed description, an example in which the knee link 12 includes a protrusion, and the connecting link 15 includes a receiver may also be possible.

The protrusion 154 may perform a rotary motion while sliding on a knee link base 121 of the knee link 12. When the connecting link 15 constructs a 4-bar linkage together with the thigh link 11, the knee link 12 and the support link 13, the protrusion 154 may perform the rotary motion within an angle range in which the protrusion 154 may not reach the receiver 122. Thus, while the motion assistance apparatus 1 of FIG. 3 is assisting the hip joint motion of the user U, the protrusion 154 may not be inserted into the receiver 122.

Meanwhile, when the connecting link 15 is disconnected from the support link 13, that is, when the connecting link 15 does not construct a 4-bar linkage together with the thigh link 11, the knee link 12 and the support link 13, the protrusion 154 may perform the rotary motion up to an angle at which the protrusion 154 reaches the receiver 122. When the protrusion 154 is inserted into the receiver 122, the connecting link 15 and the knee link 12 may be fixed to each other. The protrusion 154 may be inserted into the receiver 122 when the connecting link 15 rotates at least a preset angle. Referring to a top view of 8A, the receiver 122 may be on a lower side of the knee link 12. When the connecting link 15 is connected to the knee link 12, the protrusion 154 may perform the rotary motion on an upper semicircle of the knee link base 121, and a rotary motion of the protrusion 154 on a lower semicircle may be structurally restricted. Meanwhile, when the connecting link 15 is disconnected from the knee link 12, the protrusion 154 may rotate in a direction of an arrow toward the lower semicircle of the knee link base 121, and be inserted into the receiver 122. For example, in a case in which the connecting link 15 is rotatably connected to a right end of the knee link 12 (FIG. 3), the preset angle may exceed 180 degrees in a clockwise direction from the knee link 12. For example, the receiver 122 may be at a portion corresponding to 270 degrees in the clockwise direction from the knee link 12.

One of the knee link 12 and the connecting link 15 may include a link axis configured to pass through the other one of the knee link 12 and the connecting link 15, a support plate at an end portion of the link axis, and an elastic body between the support plate and an inner wall of the other one of the knee link 12 and the connecting link 15. For example, the connecting link 15 may include a link axis 155 configured to pass through the knee link 12, a support plate 156 at an end portion of the link axis 155, and an elastic body 157 between the support plate 156 and an inner wall 124 of the knee link 12. The elastic body 157 may be contracted while the protrusion 154 is performing a rotary motion along the knee link base 121. When the protrusion 154 is inserted into the receiver 122, the elastic body 157 may prevent a separation of the protrusion 154 from the receiver 122 by applying an elastic force to the inner wall of the knee link 12. The knee link 12 may include a link hole 123 configured to rotatably support the link axis 155.

Figure 10A:
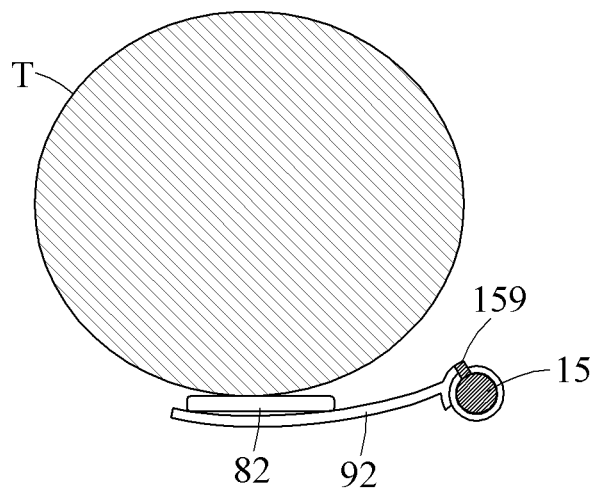
FIG. 10A is a cross-sectional view illustrating the motion assistance apparatus of FIG. 4, cut along a line I-I, in which a calf supporting frame is connected to a thigh frame.
Figure 10B:
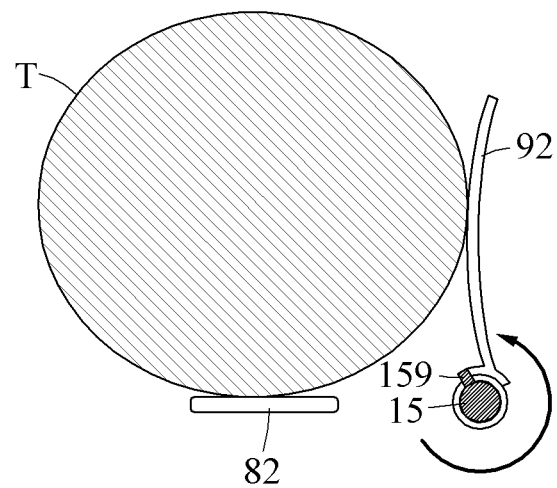
FIG. 10B is a cross-sectional view illustrating a calf supporting frame rotated about a connecting link according to at least one example embodiment.
Figure 11:
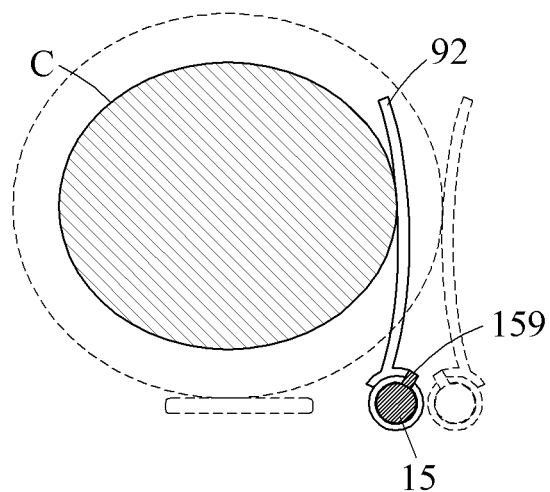
FIG. 11 is a cross-sectional view of the motion assistance apparatus of FIG. 5, cut along a line II-II, in which a calf supporting frame supports a calf of a user.

FIG. 10A is a cross-sectional view illustrating the motion assistance apparatus of FIG. 4, cut along a line I-I, in which a calf supporting frame is connected to a thigh frame. FIG. 10B is a cross-sectional view illustrating the calf supporting frame rotated about a connecting link according to at least one example embodiment. FIG. 11 is a cross-sectional view of the motion assistance apparatus of FIG. 5, cut along a line II-II, in which the calf supporting frame supports a calf of a user.

Referring to FIGS. 10A through 11, the calf supporting frame 92 may rotate about the connecting link 15. In addition, the calf supporting frame 92 may rotate about the knee link 12 as the connecting link 15 rotates about the knee link 12. FIGS. 10A and 10B illustrate the calf supporting frame 92 rotated about the connecting link 15. FIGS. 10B and 11 illustrate the calf supporting frame 92 rotated about the knee link 12. For better understanding, FIG. 10B is illustrated using broken lines in FIG. 11.

A stopper 159 and the calf supporting frame 92 may each include a permanent magnet. As a distance between the stopper 159 and the calf supporting frame 92 decreases, the stopper 159 and the calf supporting frame 92 may be maintained to be in contact with each other by magnetism. In a case in which the motion assistance apparatus 1 of FIG. 3 assists a hip joint of the user (for example, as in FIG. 10A), the calf supporting frame 92 may be maintained to be in contact with a first side of the stopper 159 by magnetism. In a case in which the motion assistance apparatus 1 assists a knee joint of the user (for example, as in FIG. 11), the calf supporting frame 92 may be maintained to be in contact with a second side of the stopper 159 by magnetism. However, a contact maintaining means for the stopper 159 and the calf supporting frame 92 is not limited thereto.

The calf supporting frame 92 may rotate about the connecting link 15. The connecting link 15 may include the stopper 159 configured to restrict a rotation range of the calf supporting frame 92. The stopper 159 may prevent a backward tilt of the calf supporting frame 92 by a reaction applied from the calf while the calf supporting frame 92 is applying a force to the calf of the user.

The calf supporting frame 92 may rotate such that the calf supporting frame 92 may change states, between a state of being in contact with the first side of the stopper 159 and a state of being in contact with the second side of the stopper 159. When supporting the calf C of the user, the calf supporting frame 92 may maintain the state of being in contact with the first side of the stopper 159. For example, the calf supporting frame 92 being in contact with the first side of the stopper 159 may rotate in a direction of an arrow and be in contact with the second side of the stopper 159. Then, the calf supporting frame 92 may rotate about the knee link 12 and support the calf C. While a front side of the calf supporting frame 92 is supporting the calf C, a rear side of the calf supporting frame 92 may be supported by a second side of the stopper 159, and the backward tilt of the calf supporting frame 92 may be prevented.

The calf supporting frame 92 may be curved in a shape enclosing the calf C of the user when in contact with the calf C of the user. The calf supporting frame 92 may stably apply a force to the calf C, and prevent a separation of the calf supporting frame 92 from the calf C. In addition, by the shape of the calf supporting frame 92, while the motion assistance apparatus 1 of FIG. 3 is assisting the hip joint of the user, the calf supporting frame 92 may enclose at least a portion of a thigh T of the user, and a separation distance between the calf supporting frame 92 and a body of the user may decrease.

Figure 12:
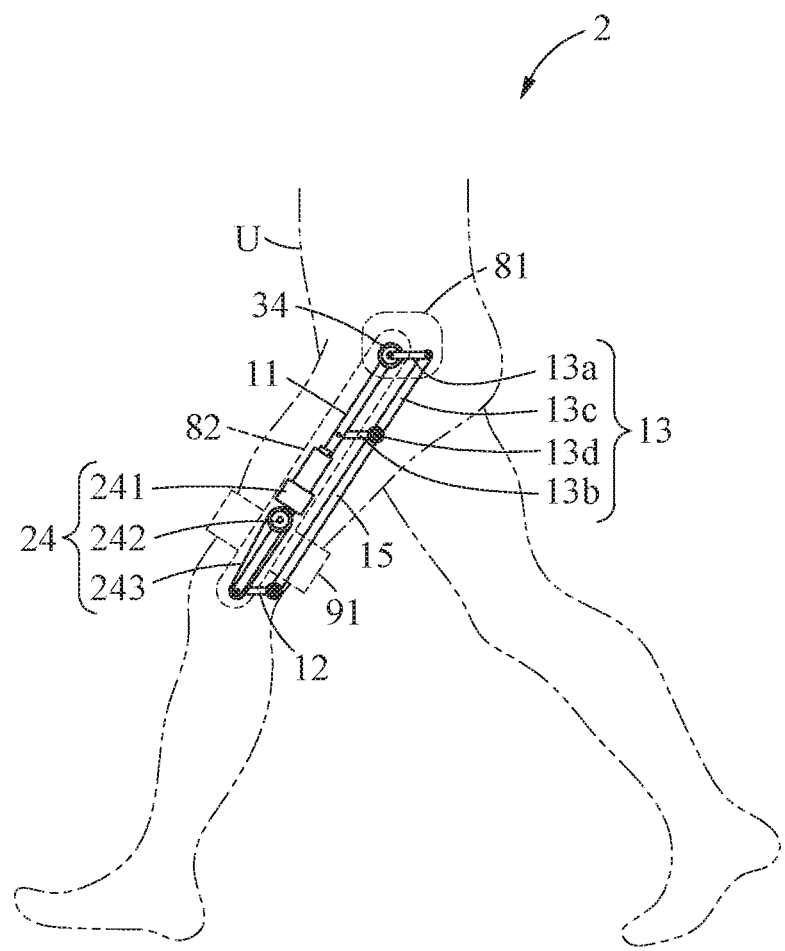
FIG. 12 illustrates a motion assistance apparatus assisting a hip joint of a user according to at least one example embodiment.
Figure 13:
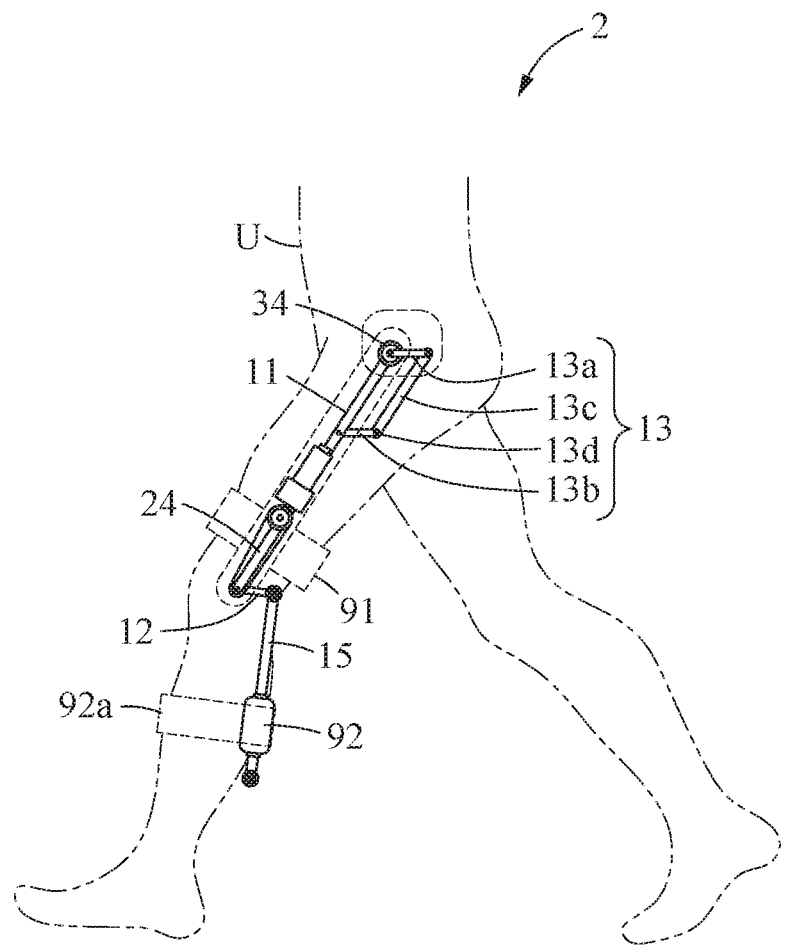
FIG. 13 illustrates a motion assistance apparatus simultaneously assisting a hip joint and a knee joint of a user according to at least one example embodiment.

FIG. 12 illustrates a motion assistance apparatus assisting a hip joint of a user according to at least one example embodiment, and FIG. 13 illustrates the motion assistance apparatus simultaneously assisting the hip joint and a knee joint of the user according to at least one example embodiment.

Referring to FIGS. 12 and 13, a motion assistance apparatus 2 may include the thigh link 11, the knee link 12, the support link 13, a first actuator 24, a second actuator 34, the connecting link 15, the waist frame 81, the thigh frame 82, the thigh attachable portion 91, and the calf supporting frame 92.

The first actuator 24 may rotate the knee link 12 with respect to the thigh link 11. The first actuator 13 may include a driving source 241, a drive shaft 242, and a power transmitting member 243. The second actuator 34 may rotate the thigh link 11 with respect to the support link 13.

When the connecting link 15 is connected to the support link 13, the first actuator 24 and the second actuator 34 may simultaneously assist a flexion motion or an extension motion of a hip joint of the user U.

When the connecting link 15 is disconnected from the support link 13, the first actuator 24 may assist a flexion or extension motion of a knee joint of the user U, and the second actuator 34 may assist the flexion or extension motion of the hip joint of the user U.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus, comprising:
   a support link configured to attach to a waist of a user, the support link including a first end and a second end;
   a thigh link connected to the first end of the support link;
   a knee link connected to the thigh link;
   a connecting link connected to the knee link, the connecting link configured to be selectively connected to the second end of the support link such that the connecting link is configured to,
      assist a hip joint motion of the user by performing a 4-bar linkage motion together with the thigh link, the knee link, and the support link, when the connecting link is connected to the support link, and
      assist a knee joint motion of the user, when the connecting link is disconnected from the support link; and
   an actuator configured to rotate the knee link with respect to the thigh link.

2. The motion assistance apparatus of claim 1, further comprising:
   a calf supporting frame rotatably connected to the connecting link, the calf supporting frame configured to support a calf of the user, when the connecting link is disconnected from the support link.

3. The motion assistance apparatus of claim 2, wherein the connecting link comprises:
   a stopper configured to restrict a rotation range of the calf supporting frame.

4. The motion assistance apparatus of claim 3, wherein the calf supporting frame is configured to,
   rotate between a first state and a second state, the first state being a state in which the calf supporting frame is in contact with a first side of the stopper and the second state being a state in which the calf supporting frame is in contact with a second side of the stopper, and
   maintain the first state of being in contact with the first side of the stopper, when the calf supporting frame is supporting a calf of the user while the connecting link is disconnected from the support link.

5. The motion assistance apparatus of claim 4, wherein the calf supporting frame is curved such that the calf supporting frame is configured to enclose the calf of the user, when the calf supporting frame is in contact with the calf of the user.

6. The motion assistance apparatus of claim 3, wherein the support link comprises:
   a first sub-support link configured to attach to the waist of the user, the first sub-support link rotatably connected to a first portion of the thigh link;
   a second sub-support link having a first end and a second end, the second sub-support link being between the first sub-support link and the knee link, the first end of the second sub-support link being rotatably connected to a second portion of the thigh link; and
   a third sub-support link configured to connect the first sub-support link and the second sub-support link, wherein
      the connecting link is configured to selectively connect to the second end of the second sub-support link.

7. The motion assistance apparatus of claim 6, wherein, when the connecting link is connected to the second end of the second sub-support link,
   the first sub-support link, the second sub-support link, and the knee link are in parallel with each other,
   the third sub-support link is in parallel with the thigh link, and
   the connecting link is in parallel with the thigh link.

8. The motion assistance apparatus of claim 1, wherein the actuator comprises:
   a driving source on the thigh link such that the driving source is closer to the support link than the knee link; and
   a power transmitting member including a band, belt or chain configured to transmit power from the driving source to the knee link.

9. The motion assistance apparatus of claim 1, wherein the support link includes a coupling pin configured to rotatably connect the connecting link to the support link, and the connecting link includes a connecting head opened toward the coupling pin, and wherein the motion assistance apparatus further comprises:
   a fixing pin configured to attach to the connecting head, the fixing pin configured to resist a separation of the coupling pin from the connecting head.

10. The motion assistance apparatus of claim 9, wherein the connecting head further includes a projection protruding toward the coupling pin, and
    the coupling pin includes a fixing groove configured to receive the fixing pin and the projection.

11. The motion assistance apparatus of claim 1, wherein one of the knee link or the connecting link includes a receiver, the receiver having a dent shape, and
    an other one of the knee link or the connecting link includes a protrusion, the protrusion configured to be inserted into the receiver.

12. The motion assistance apparatus of claim 11, wherein the protrusion is configured to align with the receiver, when the connecting link is disconnected from the support link and rotates at at least a set angle with respect to the knee link.

13. The motion assistance apparatus of claim 12, wherein the other one of the knee link or the connecting link further comprises:
    a link configured to pass through the other one of the knee link or the connecting link;
    a support plate at an end portion of the link; and an elastic body between the support plate and an inner wall of the other one of the knee link or the connecting link.

14. A motion assistance apparatus, comprising:
a support link configured to attach to a waist of a user, the support link including a first end and a second end;
a thigh link connected to the first end of the support link;
a knee link connected to the thigh link;
a connecting link connected the knee link, the connecting link configured to be selectively connected to the second end of the support link such that the connecting link is configured to,
  assist motion of a hip joint of the user by performing a 4-bar linkage motion together with the thigh link, the knee link, and the support link, when the connecting link is connected to the support link, and
  assist motion of a knee joint of the user, when the connecting link is disconnected from the support link;
a first actuator configured to rotate the knee link with respect to the thigh link; and
a second actuator configured to rotate the thigh link with respect to the support link.

15. The motion assistance apparatus of claim 14, wherein the first actuator and the second actuator are configured to assist one or more of flexion motion and an extension motion of the hip joint of the user, when the connecting link is connected to the support link.

16. The motion assistance apparatus of claim 14, further comprising:
a calf supporting frame connected to the connecting link, the calf supporting frame configured to support a calf of the user, when the connecting link is disconnected from the support link.

17. The motion assistance apparatus of claim 16, wherein, when the connecting link is disconnected from the support link,
the first actuator is configured to assist one or more of a flexion motion and an extension motion of the knee joint of the user, and
the second actuator is configured to assist one or more of a flexion motion and an extension motion of the hip joint of the user.

18. A motion assistance apparatus, comprising:
a support link configured to attach to a waist of a user, the support link including a first end and a second end;
a thigh link connected to the first end of the support link;
a knee link connected to the thigh link; and
a connecting link connected to the knee link, the connecting link configured to be selectively connected to the second end of the support link, wherein
  the motion assistance apparatus is configured to select which joint of the user is to receive an assistance force based on whether the connecting link is connected to the support link such that the motion assistance apparatus is configured to,
    assist motion of a hip joint of the user by performing a 4-bar linkage motion together with the thigh link, the knee link, and the support link, when the connecting link is connected to the support link, and
    assist motion of a knee joint of the user, when the connecting link is disconnected from the support link.

19. The motion assistance apparatus of claim 18, wherein the motion assistance apparatus is configured to,
transmit the assistance force to the hip joint, when the connecting link is connected to the support link, and
transmit the assistance force to the knee joint, when the connecting link is disconnected from the support link.

\* \* \* \* \*